(12) United States Patent
Russ et al.

(10) Patent No.: US 6,299,890 B1
(45) Date of Patent: Oct. 9, 2001

(54) MAKEUP COMPOSITIONS

(75) Inventors: Julio Gans Russ, Westfield; Ida Marie Sandewicz, Monroe Township; Tatyana Zamyatin, Princeton Junction, all of NJ (US)

(73) Assignee: Revlon Consumer Products Corporation, New York, NY (US)

( * ) Notice: Subject to any disclaimer, the term of this patent is extended or adjusted under 35 U.S.C. 154(b) by 0 days.

(21) Appl. No.: 09/469,825

(22) Filed: Dec. 22, 1999

(51) Int. Cl.$^7$ .............................. A61K 6/00; A61K 31/74
(52) U.S. Cl. ................... 424/401; 424/78.02; 424/78.03; 514/844; 514/845; 514/937; 514/938
(58) Field of Search ................................. 424/401, 78.02, 424/78.03; 514/844, 845, 937, 938

(56) References Cited

U.S. PATENT DOCUMENTS

| | | | |
|---|---|---|---|
| 4,826,809 | 5/1989 | Giesen | 514/2 |
| 5,599,533 | * 2/1997 | Stepniewski | 424/78.02 |
| 5,849,314 | 12/1998 | Dobkowski | 424/401 |
| 5,879,684 | 3/1999 | Fox | 424/195.1 |
| 5,919,468 | 7/1999 | Bara | 424/401 |
| 5,942,213 | * 8/1999 | Bara et al. | 424/63 |

FOREIGN PATENT DOCUMENTS

| | | |
|---|---|---|
| 790 055 | 8/1997 | (EP) . |
| WO 99/22696 | 5/1999 | (WO) . |

OTHER PUBLICATIONS

Vegeseryl HGP, Laboratories Seriobiologiques, $2^{nd}$ Edition, Jan. 1998.*

Vegeseryl HGP, Laboratories Seriobiologiques, Second Edition, Jan. 1, 1998.

* cited by examiner

Primary Examiner—Thurman K. Page
Assistant Examiner—S. Tran
(74) Attorney, Agent, or Firm—Julie Blackburn

(57) ABSTRACT

An emulsion makeup composition comprising:
(a) a water phase having solubilized therein an effective amount of soy protein capable of forming a skin firming and toning film on the skin;
(b) an oil phase comprising silicone oil having dispersed therein one or more colorants, said silicone oil phase capable of plasticizing the film formed on the skin by the solubilized soy protein in the water phase; and
(c) an effective amount of a surfactant capable of causing the water and oil phase to form an emulsion which maintains stability at 50° C. for two weeks.

20 Claims, No Drawings

MAKEUP COMPOSITIONS

TECHNICAL FIELD

The invention is in the field of makeup compositions for application to skin to color, condition, beautify skin as well as minimize the appearance of skin surface defects such as lines and wrinkles, and improve skin firmness and tone.

BACKGROUND OF THE INVENTION

A large majority of women wear foundation makeup and related products such as blush, eyeshadow, and concealer. Women are particularly attracted to foundation and concealer because these products are capable of minimizing skin irregularities and surface defects, and improving the appearance of facial skin and the under eye area. The most recent trend reflects the desire of women to use products that condition and beautify their skin in addition to providing cosmetic enhancement. Thus, what is referred to as "treatment makeup" has become more important in recent years. Typical treatment makeups provide benefits such as conditioning and moisturizing the skin, possibly providing UV protection, in addition to coloring the skin. Cosmetic companies are very interested in continuing to improve makeup formulas so that they provide maximum skin treatment, e.g. are "good" to the skin, while providing the cosmetic benefits desired by consumers. In particular, as women age, skin exhibits fine lines and wrinkles and loses elasticity. Loss of elasticity causes skin to sag. Consumers are particularly interested in makeup compositions that minimize the appearance of fine lines and wrinkles and provide a toning, firming effect to the skin, minimizing the appearance of skin elasticity loss.

A variety of ingredients are known to tighten loose skin and minimize the appearance of fine lines and wrinkles. Typical examples are animal derived proteins such as bovine serum albumin, and certain plant and vegetable extracts. The problem with such materials is that while they provide an excellent tightening effect to skin, when such ingredients are dispensed in the form of simple solutions or emulsions, they are not aesthetically pleasing to consumers. A consumer will not generally wear a makeup composition that is not aesthetically pleasing even if it provides extremely desirable benefits. For example, solutions and simple emulsions containing bovine serum albumin as a skin firming agent will exhibit miraculous results. However, the film formed on the skin is simply too dry and hard (inadequate plasticity), and in two hours or less, begins to crack and peel, providing a most undesirable appearance. Since most women do not wish to reapply makeup every one to two hours, the use of this material in solutions or simple emulsions is not commercially feasible. Similarly, vegetable and plant derived firming agents exhibit similar problems. Thus, the problem with such wrinkle reducing and firming agents is how to formulate them into a cosmetic composition that is aesthetically pleasing and easy for consumers to work with. Such compositions must exhibit adequate play time, meaning that the composition sets in the appropriate period of time. Too much play time means that the composition takes to long to set after it is applied to skin. Too little play time means that the composition sets too rapidly, often before the consumer manages to spread the composition onto the skin. Another requirement that must be satisfied is adequate spreadability. In other words, the composition when applied to skin must be capable of being spread to cover the skin surface. Compositions that have inadequate spreadability generally do not spread readily on the skin. Compositions having too much spreadability tend to spread too readily on the skin and do not exhibit adequate adherence to the skin surface to which they are applied. In addition, desirable compositions must permit a film to be applied to skin to cause adequate firming and toning of the skin, but the film must be sufficiently plasticized such that it does not crack or peel from the skin surface.

Accordingly, one object of the present invention is directed to a makeup composition that conditions and moisturizes skin as well as minimizing the appearance of wrinkles and fine lines, and providing a toning and firming effect to counteract the effects of skin elasticity loss that occurs with age.

Another object of the invention is to provide a makeup composition that exhibits optimum spreadability and play time, and provides a firming, toning, film on the skin which is adequately plasticized such that the film formed does not crack on, or peel off of, the skin.

Another object of the present invention is to provide a makeup composition which firms the skin, minimizes wrinkles and fine lines, and is simultaneously capable of providing UVA and UVB protection to the skin.

Another object of the present invention is to provide a makeup composition that contains soy protein rather than the animal protein derivatives traditionally used in firming makeups.

Another object of the invention is provide a makeup composition that minimizes fine lines and wrinkles, firms and tones the skin, and is stable at 50° C. after two weeks.

SUMMARY OF THE INVENTION

The invention is directed to an emulsion makeup composition comprising:

(a) a water phase having solubilized therein an effective amount of soy protein capable of forming a skin firming and toning film on the skin;

(b) an oil phase comprising silicone oil having dispersed therein one or more colorants, said silicone oil phase capable of plasticizing the film formed on the skin by the solubilized soy protein in the water phase; and (c) an effective amount of a surfactant capable of causing the water and oil phase to form an emulsion which maintains stability at 50° C. for two weeks.

DETAILED DESCRIPTION

The term "makeup composition" means a foundation makeup, blush, eyeshadow, or any other type of pigmented composition applied to the skin to provide color, or to match skin color in order to blur surface defects and improve skin irregularities.

The term "emulsion" means water-in-oil or oil-in-water emulsion, where one phase is dispersed in another, continuous phase.

I. The Water Phase

A. Water

The makeup compositions of the invention comprise 1–95%, preferably 5–80%, more preferably 10–70% by weight of the total composition of water.

B. Soy Protein

Soy Protein is solubilized in the water phase of the emulsion makeup compositions of the invention. The amount of soy protein solubilized in the aqueous phase is an amount which provides a skin firming or tightening effect to the skin when formulated into the makeup compositions of the invention and applied to the skin. Generally, the amount of soy protein that will provide a firming and tightening effect to the skin, and minimize the appearance of fine lines and wrinkles comprises about 0.01–15%, preferably 0.05–10%, more preferably 0.1–8% by weight of the total composition. The soy protein used in the compositions of the invention may be hydrolyzed or non-hydrolyzed, but is preferably non-hydrolyzed. Preferably, the soy proteins comprise both albumin and globulin fractions, which provides them with a structure similar to that of animal serum albumin. Preferably, the soy proteins have a molecular weight of about 250,000 to 700,000 daltons, and a total protein content of about 6% by weight. The soy protein may be prepared by extraction and/or purification of the seeds of renewing leguminous seeds of Glycine Soja. Particularly preferred is a soy protein sold under the tradename Vegeseryl HGP by Laboratories Sériobioloques, having the INCI name Soybean (Glycine Soya) Protein. The Vegeseryl HGP material is purchased in the form of a concentrated, colloidal hydrosolute.

C. Other Ingredients

The water phase of the composition may contain other ingredients that are soluble in the aqueous phase such as mono-, di-, or polyhydric alcohols, water soluble plant extracts, and the like.

1. Alcohols

Suitable alcohols include mono-, di-, or polyhydric alcohols such as ethanol, propanol, butylene glycol, propylene glycol, benzyl alcohol, butyl alcohol, hexanol, and the like. If one or more of these alcohols are present in the composition, a range of 0.01–10%, preferably, 0.05–8%, more preferably 0.1–5% by weight of the total composition is suggested. Particularly preferred alcohols are propylene glycol, butylene glycol, or mixtures thereof.

2. Plant Extracts

A variety of water soluble plant extracts may be solubilized in the aqueous phase. Examples of such extracts include extracts of flowers or plants such as chamomile, aloe, apple, lady's slipper, meadowsweet, lime, lemon, lilac, oat bran, mulberry root, grapefruit, saxifraga sarmentosa, tannic acid, kojic acid, and so on. Suitable ranges of water soluble plant extracts are 0.001–8%, preferably 0.005–5%, more preferably 0.01–4% by weight of the total composition. Preferred extracts are chamomile, lemon, mulberry root, grapefruit, saxifraga sarmentosa, tannic acid, kojic acid, and mixtures thereof. Particularly preferred are chamomile extract, and an extract sold by Coletica/Bioetica under the tradename Phytoclar, which is a mixture of water, mulberry root extract, butylene glycol, lemon extract, grapefruit extract, saxifraga sarmentose extract, tannic acid, kojic acid, and xanthan gum.

3. Emulsion Stabilizers

It also may be desirable to include one or more emulsion stabilizers in the aqueous phase. Suitable emulsion stabilizers are salts such as potassium chloride, sodium chloride, magnesium sulfite, ammonium chloride, and the like. If present in the composition, a suitable range for the emulsion stabilizer comprises 0.001–5%, preferably 0.005–4%, more preferably 0.1–3% by weight of the total composition. The preferred emulsion stabilizer is calcium chloride.

B. Oil Phase

The makeup compositions comprise 0.1–50%, preferably 1–30%, more preferably 5–25% by weight of the total composition of an oil phase which comprises silicone oil having dispersed therein one or more colorants. The oil phase may additionally contain one or more organic oils, provided that the silicone oil and organic oils are compatible, i.e. soluble in each other. The oil phase must adequately plasticize the dried film formed on the skin by the soy protein solubilized in the aqueous phase, such that the plasticized film does not crack or chip from the skin, or form a tough, taut film that the consumer "feels" on the skin. Rather the oil phase should cause the film to have adequate plasticity such that the film adheres to the skin, yet is plastic enough to "give" when the when the user undertakes the normal daily facial expressions. The film should be plasticized to the extent that the consumer does not feel the film on the skin. It has been found that the ranges set forth above for the oil phase provide the optimum plasticity to the dried film formed on the skin by the aqueous phase containing the solubilized soy protein.

1. Silicone Oil

The silicone oil may be volatile, non-volatile or a mixture of both, provided that the silicone oils are soluble in each other, and in the oil phase of the composition. Suitable volatile silicones include Cyclic silicones (or cyclomethicones) are of the general formula:

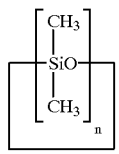

where n=3–7.

Linear volatile silicones in accordance with the invention have the general formula:

where n=0–6, preferably 0–5.

Linear and cyclic volatile silicones are available from various commercial sources including Dow Corning Corporation and General Electric. The Dow Corning volatile silicones are sold under the tradenames Dow Corning 244, 245, 344, and 200 fluids. These fluids comprise octamethylcyclotetrasiloxane, decamethylcyclopentasiloxane, hexamethyldisiloxane, and mixtures thereof.

Suitable nonvolatile silicones include water insoluble silicones having a viscosity of 10 to 600,000 centistokes, preferably 20 to 100,000 centistokes at 25° C. Suitable water insoluble silicones include cetyl dimethicone, dimethicone, phenyl trimethicone, phenyldimethicone, diphenyl dimethicone, and mixtures thereof. Such silicones are available from Dow Corning as the 3225C formulation aid, Dow 190 and 193 fluids, or similar products marketed by Goldschmidt under the ABIL tradename.

Also suitable as the nonvolatile silicone oil are various fluorinated silicones such as trimethylsilyl endcapped fluorosilicone oil, polytrifluoropropylmethylsiloxanes, and similar silicones such as those disclosed in U.S. Pat. No. 5,118, 496 which is hereby incorporated by reference.

Preferably, the makeup compositions comprise a mixture of volatile and non-volatile silicones, in particular, about 0.5–20% by weight of the total composition of volatile silicone oil, and about 0.5–15% nonvolatile silicone. The presence of the volatile silicone enables the makeup to dry on the skin in an appropriate period of time, and minimizes the heavy, greasy feel that is occasionally found with non-volatile oils. The remaining nonvolatile oil phase acts to plasticize the film formed on the skin by the dried aqueous phase containing the solubilized soy protein.

B. Colorants

Dispersed in the oil phase of the composition are one or more colorants. Suitable colorants may be inorganic or organic pigments and powders. The organic pigments are generally various aromatic types including azo, indigoid, triphenylmethane, anthraquinone, and xanthine dyes which are designated as D&C and FD&C blues, browns, greens, oranges, reds, yellows, etc. Organic pigments also generally consist of insoluble metallic salts of certified color additives, referred to as the Lakes. Inorganic pigments include iron oxides, ultramarines, chromium, chromium hydroxide colors, and mixtures thereof. Preferably, the pigments may be coated with one or more ingredients that cause the pigments to be hydrophobic. Suitable coating materials that will render the pigments more lipophilic in nature include silicones, lecithin, amino acids, phospholipids, inorganic and organic oils, polyethylene, and other polymeric materials. Particularly preferred are silicone treated pigments as disclosed in U.S. Pat. No. 5,143,722, which is hereby incorporated by reference.

C. Other Ingredients

The oil phase may contain additional ingredients that are soluble or dispersible in the oil phase, such as waxes, oil soluble synthetic polymers, particulates, and so on.

1. Particulates

The oil phase preferably contains one or more particulates which serve as powders, fillers, or sunscreens in the composition. These powders or fillers are present for adjusting the color of the composition, and in some cases may provide a sunscreen effect by physical blocking of UV radiation. Preferably, the particle size of the particulates ranges from 0.05 to 100 microns, and are present in ranges of 0.1–20%, preferably 0.5–15%, more preferably 1–10% by weight of the total composition. Examples of particulates include white or non-pigmentitious powders include bismuth oxychloride, titanated mica, fumed silica, spherical silica, polymethylmethacrylate, micronized teflon, boron nitride, acrylate copolymers, aluminum silicate, aluminum starch octenylsuccinate, bentonite, calcium silicate, cellulose, chalk, corn starch, diatomaceous earth, fuller's earth, glyceryl starch, hectorite, hydrated silica, kaolin, magnesium aluminum silicate, magnesium trisilicate, maltodextrin, montmorillonite, microcrystalline cellulose, rice starch, silica, talc, mica, titanium dioxide, zinc laurate, zinc myristate, zinc rosinate, alumina, attapulgite, calcium carbonate, calcium silicate, dextran, kaolin, nylon, silica sylilate, silk powder, sericite, soy flour, tin oxide, titanium hydroxide, trimagnesium phosphate, walnut shell powder, or mixtures thereof. While titanium dioxide is commonly considered to be a white pigment when used in paints, in color cosmetic compositions it is used more for its ability to mute color, and/or provide an opaque or semi-opaque finish, or provide sunscreen protection, then as a colorizing ingredient. The above mentioned particulates may be surface treated with lecithin, amino acids, mineral oil, silicone oil or various other agents either alone or in combination, which coat the powder surface and render the particles more lipophilic in nature.

It is particularly preferred that the compositions of the invention comprise very fine particle zinc oxide and/or titanium dioxide, in addition to the other pigments and particulates which may be present. The mixture of zinc oxide and titanium dioxide causes the makeup composition to exhibit a very high sun protective factor (SPF), as high as 15 to 20 SPF. Preferred particle sizes of the zinc oxide and titanium dioxide are 0.005 to 10 microns. Preferably the compositions of the invention contain 1–15% by weight of the composition of zinc oxide, titanium dioxide, or mixtures thereof, having a particle size of 0.005 to 10 microns and providing makeup having an SPF of 15 to 20, preferably 20.

2. Organic Oils

The oil phase may additionally comprise one or more organic oils, if desired, provided the organic oils selected are soluble in the silicone oil phase and contribute to plasticizing the film formed on the skin by the dried soy protein.

Examples of suitable organic oils include hydrocarbons, esters, and the like. Suitable hydrocarons include paraffinic hydrocarbons having 9 to 70 carbon atoms, C20–45 olefins, isododecane, isobutene, isoeicosane, isohexadecane, mineral oil, squalene, squalane, and the like.

Also suitable are various esters that are liquid at room temperature. Suitable esters include guerbet esters, which are generally defined as esters which are formed by the reaction of a guerbet alcohol (which is a branched chain alcohol) having the general formula:

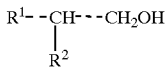

with a carboxylic acid having the general formula:

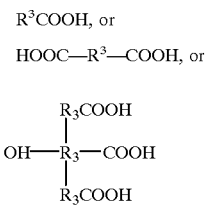

wherein $R^1$ and $R^2$ are each independently a $C_{4-20}$ alkyl and each $R^3$ is a substituted or unsubstituted $C_{1-50}$ straight or branched chain alkyl or alkylene group, or phenyl, wherein the substituents are halogen, hydroxyl, carboxyl, or alkylcarbonyloxy.

Other suitable esters include those having the formula RCO—OR' wherein R and R' are each independently a $C_{1-25}$, preferably a $C_{4-20}$, straight or branched chain alkyl, alkenyl or alkoxycarbonylalkyl or alkylcarbonyloxyalkyl. Preferred are esters which are the reaction product of of a branched chain fatty acid and a branched or straight chain fatty alcohol, preferably a branched chain fatty alcohol. Examples of such esters include isotridecyl isononanoate, isostearyl neopentanoate, tridecyl neopentanoate, cetyl octanoate, cetyl ricinoleate, decyl isostearate, isodecyl oleate, isodecyl neopentanoate, isohexyl neopentanoate, tridecyl octanoate, and so on.

Other suitable esters include naturally occuring glyceryl esters of fatty acids, or triglycerides. Both vegetable and animal sources may be used. Examples of such oils include castor oil, lanolin oil, triisocetyl citrate, $C_{10-18}$ triglycerides, caprylic/capric/triglycerides, coconut oil, corn oil, cottonseed oil, linseed oil, mink oil, olive oil, palm oil, illipe butter, rapeseed oil, soybean oil, sunflower seed oil, walnut oil, and the like.

Also suitable are synthetic or semi-synthetic glyceryl esters, e.g. fatty acid mono-, di-, and triglycerides which are natural fats or oils that have been modified, for example, acetylated castor oil, glyceryl stearate, glyceryl dioleate, glyceryl distearate, glyceryl trioctanoate, glyceryl linoleate, glyceryl myristate, glyceryl isostearate, PEG castor oils, PEG glyceryl oleates, PEG glyceryl stearates, PEG glyceryl tallowates, and so on.

3. Waxes

The compositions may also contain one or more waxes which are solid or semi-solid at room temperature, provided such waxes and soluble or miscible with the oil phase when the wax and the oil phase are heated together to a temperature sufficient to melt the wax. Suggested ranges of wax are 0.1–20%, preferably 0.5–15%, more preferably 1–10% by weight of the total composition. The waxes preferably have a melting point of about 39 to 135° C., preferably in the range of 45 to 95° C., most preferably 55 to 95° C. Suitable waxes generally include animal waxes, plant waxes, mineral waxes, silicone waxes, synthetic waxes, and petroleum waxes. More specifically, these waxes include tribehenin, bayberry, beeswax, candelilla, carnauba, ceresin, cetyl esters, hydrogenated jojoba oil, hydrogenated jojoba wax, hydrogenated microcrystalline wax, hydrogenated rice bran wax, japan wax, jojoba butter, jojoba esters, jojoba wax, lanolin wax, microcrystalline wax, mink wax, montan acid wax, montan wax, ouricury wax, ozokerite, paraffin, cetyl alcohol, beeswax, PEG-20 sorbitan beeswax, PEG-8 beeswax, rice bran wax, shellac wax, spent grain wax, sulfurized jojoba oil, synthetic beeswax, synthetic candelilla wax, synthetic carnauba wax, synthetic japan wax, synthetic jojoba oil, synthetic wax, polyethylene, stearoxy dimethicone, dimethicone behenate, stearyl dimethicone, and the like, as well synthetic homo- and copolymer waxes such as PVP/eicosene copolymer, PVP/hexadecene copolymer, and the like. Particularly preferred is where the wax is an organic wax, tribehenin.

III. Surfactant

The compositions of the invention comprise an effective amount of a surfactant which is capable of causing the water phase and the oil phase to form an emulsion having stability for two weeks at 50° C. Suggested ranges of surfactant are in the range of about 0.1–20%, preferably 0.5–15%, more preferably 1–10% by weight of the total composition of one or more surfactants. Suitable surfactants include organic or silicone surfactants, which may be anionic, cationic, nonionic, zwitterionic, or amphoteric. Preferably the surfactants are nonionic organic or silicone surfactants.

Examples of nonionic organic surfactants include alkoxylated alcohols, or ethers, formed by the reaction of an alcohol with an alkylene oxide, usually ethylene or propylene oxide. Preferably the alcohol is either a fatty alcohol having 6 to 30 carbon atoms. Examples of such ingredients include Beheneth 5–30, which is formed by the reaction of behenyl alcohol and ethylene oxide where the number of repeated ethylene oxide units is 5 to 30; Ceteareth 2–100, formed by the reaction of a mixture of cetyl and stearyl alcohol with ethylene oxide, where the number of repeating ethylene oxide units in the molecule is 2 to 100; Ceteth 1–45 which is formed by the reaction of cetyl alcohol and ethylene oxide, and the number of repeating ethylene oxide units is 1 to 45, laureth, 1–100 where the number of repeating ethylene oxide units is 1 to 100, and so on. Other alkoxylated alcohols are formed by the reaction of fatty acids and mono-, di- or polyhydric alcohols with an alkylene oxide. For example, the reaction products of $C_{6-30}$ fatty carboxylic acids and polyhydric alcohols which are monosaccharides such as glucose, galactose, methyl glucose, and the like, with an alkoxylated alcohol.

Also suitable as the nonionic surfactant are alkyoxylated carboxylic acids, which are formed by the reaction of a carboxylic acid with an alkylene oxide or with a polymeric ether. The resulting products have the general formula:

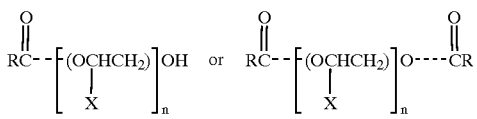

where RCO is the carboxylic ester radical, X is hydrogen or lower alkyl, and n is the number of polymerized alkoxy groups. In the case of the diesters, the two RCO-groups do not need to be identical. Preferably, R is a $C_{6-30}$ straight or branched chain, saturated or unsaturated alkyl, and n is from 1–100.

Also suitable as the nonionic surfactant are monomeric, homopolymeric and block copolymeric ethers. Such ethers are formed by the polymerization of monomeric alkylene oxides, generally ethylene or propylene oxide. Such polymeric ethers have the following general formula:

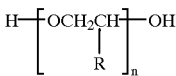

wherein R is H or lower alkyl and n is the number of repeating monomer units, and ranges from 1 to 500.

Other suitable nonionic surfactants include alkoxylated sorbitan and alkoxylated sorbitan derivatives. For example, alkoxylation, in particular, ethoxylation, of sorbitan provides polyalkoxylated sorbitan derivatives. Esterification of polyalkoxylated sorbitan provides sorbitan esters such as the polysorbates. Examples of such ingredients include Polysorbates 20–85, sorbitan oleate, sorbitan palmitate, sorbitan sesquiisostearate, sorbitan stearate, and so on.

Also suitable as nonionic surfactants are silicone surfactants, which are defined as silicone polymers which have at least one hydrophilic radical and at least one lipophilic radical. The silicone surfactant used in the compositions of the invention are organosiloxane polymers that may be a liquid or solid at room temperature. The organosiloxane surfactant is generally a water-in-oil or oil-in-water type surfactant which is, and has an Hydrophile/Lipophile Balance (HLB) of 2 to 18. Preferably the organosiloxane is a nonionic surfactant having an HLB of 2 to 12, preferably 2 to 10, most preferably 4 to 6. The HLB of a nonionic surfactant is the balance between the hydrophilic and lipophilic portions of the surfactant and is calculated according to the following formula:

$$HLB = 7 + 11.7 \times \log M_w/M_o$$

where $M_w$ is the molecular weight of the hydrophilic group portion and $M_o$ is the molecular weight of the lipophilic group portion.

The polymeric organosiloxane surfactant used in the invention may have any of the following general formulas:

$$M_xQ_y, \text{ or}$$

$$M_xT_y, \text{ or}$$

$$MD_xD'_yD''_zM$$

wherein each M is independently a substituted or unsubstituted trimethylsiloxy endcap unit. If substituted, one or more of the hydrogens on the endcap methyl groups are substituted, or one or more methyl groups are substituted with a substituent that is a lipophilic radical, a hydrophilic radical, or mixtures thereof. T is a trifunctional siloxy unit having the empirical formula $RR'SiO_{1.5}$ or $RRSiO_{1.5}$. Q is a quadrifunctional siloxy unit having the empirical formula $SiO_2$, and D, D', D", x, y, and z are as set forth below, with the proviso that the compound contains at least one hydrophilic radical and at least one lipophilic radical. Preferred is a linear silicone of the formula:

$$MD_xD'_yD''_zM$$

wherein $M=RRRSiO_{1/2}$

D and $D'=RR'SiO_{2/2}$ $D''=RRSiO_{2/2}$ x, y, and z are each independently 0–1000, where R is methyl or hydrogen, and R' is a hydrophilic radical or a lipophilic radical, with the proviso that the compound contains at least one hydrophilic radical and at least one lipophilic radical.

Most preferred is wherein

M=trimethylsiloxy $D=Si[(CH_3)][(CH_2)_nCH_3]O_{2/2}$ where n=0–40, $D'=Si[(CH_3)][(CH_2)_o-O-PE)]O_{2/2}$ where PE is $(-C_2H_4O)_a(-C_3H_6O)_bH$, o=0–40, a=1–100 and b=1–100, and $D''=Si(CH_3)_2O_{2/2}$ More specifically, suitable silicone surfactants have the formula:

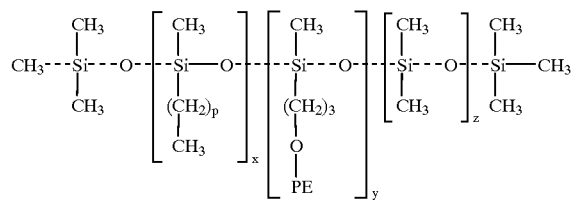

wherein p is 0–40, and

PE is $(-C_2H_4O)_a(-C_3H_6O)_b-H$ where x, y, z, a, and b are such that the maximum molecular weight of the polymer is approximately 50,000.

Another type of preferred organosiloxane emulsifier suitable for use in the compositions of the invention are emulsifiers sold by Union Carbide under the Silwet™ trademark, which are referred to by the CTFA term "dimethicone copolyol."

Also suitable as nonionic silicone surfactants are hydroxy-substituted silicones such as dimethiconol, which is defined as a dimethyl silicone substituted with terminal hydroxy groups.

Examples of silicone surfactants are those sold by Dow Corning under the tradename Dow Corning 3225C Formulation Aid, Dow Corning 190 Surfactant, Dow Corning 193 Surfactant, Dow Corning Q2-5200, and the like are also suitable. In addition, surfactants sold under the tradename Silwet by Union Carbide, and surfactants sold by Troy Corporation under the Troysol tradename, those sold by Taiwan Surfactant Co. under the tradename Ablusoft, those sold by Hoechst under the tradename Arkophob, are also suitable for use in the invention.

In the preferred compositions of the invention, the nonionic surfactant is selected from an nonionic organic surfactant, in particular, an alkoxylated alcohol; a silicone surfactant; and mixtures thereof.

IV. Other Ingredients

The compositions of the invention may contain other ingredients such as preservatives, antioxidants, vitamins, and so on.

A. Preservatives

The composition may contain 0.0001–8%, preferably 0.001–6%, more preferably 0.005–5% by weight of the total composition of preservatives. A variety of preservatives are suitable, including such as benzoic acid, benzyl alcohol, benzylhemiformal, benzylparaben, 5-bromo-5-nitro-1,3-dioxane, 2-bromo-2-nitropropane-1,3-diol, butyl paraben, calcium benzoate, calcium propionate, captan, chlorhexidine diacetate, chlorhexidine digluconate, chlorhexidine dihydrochloride, chloroacetamide, chlorobutanol, p-chloro-m-cresol, chlorophene, chlorothymol, chloroxylenol, propyl paraben, methyl paraben, benzoic acid, m-cresol, o-cresol, DEDM Hydantoin, DEDM Hydantoin dilaurate, dehydroacetic acid, diazolidinyl urea, dibromopropamidine diisethionate, DMDM Hydantoin, and all of those disclosed on pages 570 to 571 of the CTFA Cosmetic Ingredient Handbook, Second Edition, 1992, which is hereby incorporated by reference.

B. Vitamins and Antioxidants

The compositions of the invention may contain vitamins and/or coenzymes, as well as antioxidants. If so, 0.001–10%, preferably 0.01–8%, more preferably 0.05–5% by weight of the total composition are suggested. Suitable vitamins include the B vitamins such as thiamine, riboflavin, pyridoxin, and so on, as well as coenzymes such as thiamine pyrophoshate, flavin adenin dinucleotide, folic acid, pyridoxal phosphate, tetrahydrofolic acid, and so on. Also Vitamin A and derivatives thereof are suitable. Examples are Vitamin A palmitate, acetate, or other esters thereof, as well as Vitamin A in the form of beta carotene. Also suitable is Vitamin E and derivatives thereof such as Vitamin E acetate, nicotinate, or other esters thereof. In addition, Vitamins D, C, and K, as well as derivatives thereof are suitable. Particularly preferred are derivatives of vitamins C, E, and A such as magnesium ascorbyl phosphate, retinyl palmitate, tocopheryl acetate, and mixtures thereof.

Suitable antioxidants are ingredients which assist in preventing or retarding spoilage. Examples of antioxidants suitable for use in the compositions of the invention are potassium sulfite, sodium bisulfite, sodium erythrobate, sodium metabisulfite, sodium sulfite, propyl gallate, cysteine hydrochloride, butylated hydroxytoluene, butylated hydroxyanisole, and so on.

The invention will be further described in connection with the following examples that are set forth for the purposes of illustration only.

EXAMPLE 1

A makeup composition was made according to the following formula:

| | w/w % |
|---|---|
| Cyclomethicone | 3.00 |
| Propyl paraben/laureth-7 | 0.75 |
| Mica/methicone | 0.01 |
| Red iron oxide/methicone | 2.70 |
| Yellow iron oxide/methicone | 2.70 |
| Black iron oxide/methicone | 2.70 |
| Titanium dioxide/cyclomethicone/dimethicone copolyol | 14.10 |
| Zinc oxide/cyclomethicone/dimethicone copolyol | 5.00 |
| Cyclomethicone/Titanium dioxide/dimethicone copolyol/triethoxy caprylyl silane | 3.80 |
| Spherical silica | 0.15 |
| Nylon-12 | 1.00 |
| Boron nitride | 1.05 |
| Titanium dioxide/methicone | 1.00 |
| Dimethicone | 7.25 |
| Cyclomethicone | 5.80 |
| Tribehenin | 0.10 |
| Retinyl palmitate | 0.01 |
| Tocopheryl acetate | 0.01 |
| Aloe extract | 0.01 |
| Dimethicone | 1.50 |
| Polyglyceryl-4-isostearate | 1.50 |
| Cyclomethicone/dimethicone | 3.40 |
| Water | 31.05 |
| Salicylic acid/hydrolyzed vegetable protein | 0.50 |
| Methoxypropylgluconamide | 0.50 |
| Magnesium ascorbyl phosphate | 0.01 |
| Ethyl paraben/propylene glycol | 5.75 |
| Propylene glycol | 2.37 |
| Tetrasodium EDTA | 0.01 |
| Magnesium sulfate | 0.01 |
| Chamomile extract | 0.01 |
| Phytoclar | 0.01 |
| Soy protein | 3.00 |
| Cyclomethicone/dimethiconol | 2.00 |
| Methyl dihydrojasmonate | 0.25 |

The composition was prepared by combining the ingredients and mixing well to form an emulsion. The resulting makeup composition was poured into containers.

While the invention has been described in connection with the preferred embodiment, it is not intended to limit the scope of the invention to the particular form set forth but, on the contrary, it is intended to cover such alternatives, modifications, and equivalents as may be included within the spirit and scope of the invention as defined by the appended claims.

We claim:

1. An emulsion makeup composition comprising:
    (a) a water phase consisting essentially of 0.05–15% by weight of the total composition of solubilized soy protein capable of forming a skin firming and toning film on the skin and an ingredient selected from the group consisting of monohydric alcohol, dihydric alcohol, polyhydric alcohol, water soluble plant extract, emulsion stabilizer, and mixtures thereof;
    (b) an oil phase comprising silicone oil having dispersed therein one or more colorants, said silicone oil phase capable of plasticizing the film formed on the skin by the solubilized soy protein in the water phase; and
    (c) an effective amount of a surfactant capable of causing the water and oil phase to form an emulsion which maintains stability at 50° C. for at least two weeks.

2. The composition of claim 1 containing 1–95% water phase.

3. The composition of claim 2 wherein the soy protein is non-hydrolyzed.

4. The composition of claim 3 wherein the soy protein contains a mixture of albumin and globulin fractions.

5. The composition of claim 1 comprising 0.1–50% of an oil phase comprising a silicone oil.

6. The composition of claim 5 wherein the silicone oil is a volatile silicone, a non-volatile silicone, or mixtures thereof.

7. The composition of claim 6 wherein the volatile silicone is cyclomethicone and the nonvolatile silicone is dimethicone.

8. The composition of claim 5 wherein the oil phase has dispersed therein 0.1–25% by weight of the total composition of pigments.

9. The composition of claim 8 wherein the pigments are surface treated with an ingredient that confers lipophilicity.

10. The composition of claim 9 wherein the pigment is surface treated with silicone.

11. The composition of claim 5 wherein the oil phase additionally comprises 0.1–20% of white or non-pigmentitious powders having a particle size of 0.05 to 100 microns.

12. The composition of claim 11 wherein the white or non-pigmentitious powders include zinc oxide, titanium dioxide, or mixtures thereof, having a particle size of 0.05 to 10 microns.

13. The composition of claim 12 having an SPF of 15 to 20.

14. The composition of claim 1 comprising 0.1–20% by weight of the total composition of surfactant.

15. The composition of claim 14 wherein the surfactant is a nonionic surfactant.

16. The composition of claim 15 wherein the surfactant is selected from the group consisting of a nonionic organic surfactant, a nonionic silicone surfactant, and mixtures thereof.

17. The composition of claim 16 wherein the nonionic organic surfactant comprises an alkoxylated alcohol.

18. The composition of claim 16 wherein the nonionic organic surfactant comprises dimethicone copolyol.

19. The composition of claim 1 which is a water in oil emulsion.

20. An emulsion makeup composition comprising:
    (a) a water phase consisting essentially of 0.05–15% by weight of the total composition of solubilized soy protein capable of forming a skin firming and toning film on the skin;
    (b) an oil phase comprising silicone oil having dispersed therein one or more colorants, said silicone oil phase capable of plasticizing the film formed on the skin by the solubilized soy protein in the water phase; and
    (c) an effective amount of a surfactant capable of causing the water and oil phase to form an emulsion which maintains stability at 50° C. for at least two weeks.

* * * * *